United States Patent [19]
Wenzel et al.

[11] 4,206,143
[45] Jun. 3, 1980

[54] METHOD FOR MAKING N-SUBSTITUTED ACRYLAMIDES AND METHACRYLAMIDES

[75] Inventors: Franz Wenzel, Darmstadt; Peter J. Arndt, Seeheim-Jugenheim; Fritz Schlosser, Darmstadt-Kranichstein; Siegmund Besecke, Darmstadt; Heinz-Juergen Hohage, Nieder-Ramstadt-Trautheim; Guenter Schroeder, Ober-Ramstadt, all of Fed. Rep. of Germany

[73] Assignee: Röhm GmbH, Darmstadt, Fed. Rep. of Germany

[21] Appl. No.: 30,657

[22] Filed: Apr. 16, 1979

[30] Foreign Application Priority Data

Apr. 17, 1978 [DE] Fed. Rep. of Germany ....... 2816516

[51] Int. Cl.² ............................................. C07C 103/58
[52] U.S. Cl. .............................. 260/561 N; 260/562 R
[58] Field of Search ......................... 260/561 N, 562 R

[56] References Cited

U.S. PATENT DOCUMENTS

| 2,451,436 | 10/1948 | Erickson | 260/561 |
|---|---|---|---|
| 2,529,838 | 11/1950 | Erickson | 260/561 |
| 2,719,175 | 9/1955 | Coover | 260/561 |

FOREIGN PATENT DOCUMENTS

| 1965308 | 7/1970 | Fed. Rep. of Germany | 260/561 |
|---|---|---|---|
| 2347615 | 1/1975 | Fed. Rep. of Germany | 260/561 |
| 2502247 | 7/1975 | Fed. Rep. of Germany | 260/561 |
| 2752109 | 1/1978 | Fed. Rep. of Germany | 260/561 |
| 1244567 | 9/1971 | United Kingdom | 260/561 |

Primary Examiner—Arthur P. Demers
Attorney, Agent, or Firm—Curtis, Morris & Safford

[57] ABSTRACT

What is disclosed is the method for making an N-substituted acrylamide or an N-substituted methacrylamide which comprises reacting an alkyl ester of acrylic acid or of methacrylic acid with an aliphatic amine or with an aromatic amine at a temperature between 50° C. and 180° C. in the presence of a catalytic amount of a dialkyl tin oxide.

3 Claims, No Drawings

METHOD FOR MAKING N-SUBSTITUTED ACRYLAMIDES AND METHACRYLAMIDES

The present invention relates to a method for making N-substituted acrylamides or N-substituted methacrylamides.

The lower esters of acrylic acid and methacrylic acid are preferred starting materials for the preparation of other derivatives of acrylic acid and methacrylic acid because of their good availability. N-substituted amides of these acids can also be prepared from the aforementioned esters by reaction with the corresponding amines. However, amines react more easily with the carbon-carbon double bond of acrylic acid esters or methacrylic acid esters by a Michael-addition than with the ester group by aminolysis. Thus, if one reacts one mol of an acrylic ester or methacrylic ester with one mol of an amine, the corresponding $\beta$-amino-propionic acid ester or $\beta$-amino-isobutyric acid ester is obtained as the main product at moderate reaction temperatures. These addition products are unstable at temperatures above 200° C. and split off the added amine with regeneration of the carbon-carbon double bond. However, the aminolysis of the ester groups still runs its course at these temperatures.

In order to exclude the undesired Michael-addition, esters of acrylic acid or of methacrylic acid are reacted in the prior art with amines at 300° C. to 550° C. in the gas phase on solid catalysts such as vanadium-aluminum oxides with contact times of several seconds to form the corresponding substituted acrylamides or methacrylamides. The high reaction temperature favors uncontrolled decomposition and polymerization reactions, so that yields of at most 50 percent are obtained.

Other prior art teaches that at somewhat lower temperatures, namely at 150° C. to 400° C., N,N-dialkylacrylamides are obtained by the reaction of lower acrylic acid esters with higher secondary amines. Also in this process, a yield of only about 20 percent is reached.

Because of the unavoidable side reactions at high temperatures, two-stage methods for the preparation of N-substituted acrylic acid amides or methacrylic acid amides have proved to be superior. According to one prior art process, one mol of an acrylic acid ester or methacrylic acid ester is reacted in a first reaction stage with two mols of an amine at a temperature below 200° C. In this way, the Michael addition and the aminolysis occur concurrently so that the corresponding $\beta$-aminopropionamide or $\beta$-amino-isobutyramide is formed as an intermediate product. In the second reaction step, the amine added to the double bond is again split off at temperature over 200° C., whereupon the substituted acrylamide or methacrylamide is formed.

According to one prior art source, the second step of this reaction already takes place at temperatures of 100° C. to 250° C. if one works in the presence of a strong acid which binds the cleaved amine in salt form.

The last-described processes are unsatisfactory because of the multi-stage operation.

The present invention has as its object the improvement of the preparation of N-substituted amides of acrylic acid or of methacrylic acid from the esters of these acids by aminolysis, and in particular to reduce the expenditure of work and to increase the yield.

This object has been attained according to the present invention by the reaction of the aforementioned starting materials at temperatures between 50° C. and 180° C. in the presence of catalytic amounts of a dialkyl tin oxide. This catalyst has the surprising effect that it accelerates the aminolysis of the ester group to such a degree that the rate of this reaction far exceeds the velocity of the Michael-addition and the Michael-adduct arises as a by-product only in subordinate amounts.

Dialkyl tin oxide is known as a trans-esterification catalyst. For example, it catalyzes the reaction of methyl methacrylate with dimethylaminoethanol with the formation of dimethylaminoethyl methacrylate. It was not to be foreseen that this catalyst would also accelerate the aminolysis of these esters. In the process of the invention, commercially available dibutyl tin oxide is preferably used as the catalyst. However, other dialkyl tin oxides are suitable. They can, for example, contain from 1 to 12 carbon atoms in each alkyl group. The catalyst can be added in an amount from 0.1 to 10 percent, by weight of the reaction mixture, for example. In general, amounts from 0.5 to 2 percent give the most advantageous results. Dialkyl tin oxides in which each alkyl group has 4 to 8 carbon atoms are preferred.

As acrylic acid esters or methacrylic acid esters, methyl acrylate, ethyl acrylate, and methyl methacrylate are preferred because they are readily available technically and because the alcohol released on aminolysis can be easily removed from the reaction mixture. As the number of carbon atoms in the alcohol group increases, the suitability of the ester decreases. From this point of view, alkyl esters having more than four carbon atoms in the alkyl group are to be viewed as less suitable.

The aminolysis according to the invention is preferably carried out with aliphatic amines having from 2 to 20 carbon atoms. The term "aliphatic amines" is to be understood as referring to amines in which the amine nitrogen atom is bound to an aliphatic carbon atom. For example, according to this meaning those araliphatic amines such as benzyl amine are to be included among the aliphatic amines. Primary amines in general react more easily than do secondary amines and are therefore preferred. Aromatic amines, for example aniline, can also be reacted. Also here, primary amines having up to 20 carbon atoms are preferred.

The reaction is facilitated if the amine boils above the boiling point of the reaction mixture under the pressure at which the process is carried out, since in this way the alcohol released by aminolysis during the reaction can be removed azeotropically with a portion of the ester without escape of a significant amount of the amine. Amines having a boiling point about 100° C. (at normal pressure) are thus particularly suitable for the process of the invention.

The reacted amines can contain further functional groups in addition to the primary or secondary amino group. Compounds having two or more primary or secondary amino groups give the corresponding bis-, tris-, or higher acrylamides by plural aminolysis. The amines can further contain one or more tertiary amino groups, hydroxy groups, thiol groups, ether groups, or thioether groups. Thus, for example, an hydroxy group can react with a further molecule of acrylic ester or methacrylic ester by transesterification.

In a preferred embodiment of the invention, a tertiary amino alkyl amine of the general formula H$_2$N-R-NR'R" can be used as the amine, wherein R preferably is a straight-chain or branched-chain alkylene group having 2 to 4 carbon atoms and R' and R", taken alone, are the same or different alkyl groups having 1 to 8 carbon atoms, preferably 1 to 4 carbon atoms, or, taken together with the tertiary nitrogen atom, form a piperidino-, morpholino- or piperazino group. Preferably, γ-dimethylamino-propylamine is used.

Formally, equimolar amounts of the reaction partners react to form the desired end product. In practice, however, it has proved more suitable constantly to maintain the ester in excess during the reaction. For example, the amine is added gradually under the reaction conditions to the ester, which contains the catalyst. Advantageously, one operates at the boiling temperature under normal pressure, whereupon a mixture of the ester and of the cleaved alcohol are distilled off. For this reason the amount of the ester must either be set initially at such a high value that an excess of the ester can be maintained during the reaction period despite losses due to distillation, or the ester is continually added together with the amine. It is less suitable to carry out the reaction with total reflux or below the boiling temperature, since in this case the cleaved alcohol cannot be removed from the reaction mixture. The alcohol/ester mixture which is distilled off can be worked up in a manner known per se and the ester can be used again in a later batch.

Working in the manner described, the reaction temperature adjusts itself, according to the boiling point of the ester used and that of the alcohol cleaved, at a value between 50° C. and 180° C. As a rule, the reaction takes place predominantly or entirely at a reaction temperature below 120° C., preferably below 100° C. Toward the end of the reaction, when the alcohol cleavage diminishes and the concentration of the ester in the reaction mixture decreases, the reaction temperature can be increased to 150° C. Higher temperatures encourage the formation of undesired polymers.

The crude reaction product contains the N-substituted acrylamide in a yield of at least more than 90 percent, calculated on the amine employed. As a rule, small amounts of the Michael-adduct formed between the ester and the amine or between the substituted amide and the amine are contained in the crude product as by-products. Although in many cases the crude product can be used directly for the production of polymerization products, as a rule a purification by recrystallization or distillation is performed. For this, fot the most part no fractionation column is necessary If the distillation is carried out at reduced pressure at a boiling point of about 150° C. to 200° C., the desired end product is obtained in high purity after a short initial run, in which case the by-products of the reaction are for the most part decomposed. In the mode of operation which has been described, N-(dimethylaminopropyl)-methacrylamide, for example, can be obtained as a product which is 99.5 percent pure in a yield of about 95 percent of theory, calculated on the dimethylaminopropylamine added.

For avoiding polymerization losses, it is suitable to carry out the reaction and the working up of the reaction mixture in the presence of polymerization inhibitors such as phenothiazine.

A better understanding of the present invention and of its many advantages will be had by referring to the following specific Example, given by way of illustration.

EXAMPLE 1

80 kg of methyl methacrylate, 1.4 kg of dibutyl in oxide, and 40 g of phenothiazine are present in a vessel with a distillation attachment and are heated to boiling with the introduction of air. Then, 5 kg of dimethylaminopropylamine are rapidly added and the batch is heated at reflux until the temperature at the head of the reflux condenser is about 70° C. Then dimethylpropylamine is added over a period of 90 minutes until a total amount of 20.4 kg has been added. At the same time an azeotropic mixture of methanol and methylmethacrylate is distilled off at a reflux ratio of 2:1. This distillation takes up to two hours from the end of the amine addition. Subsequently the unused methyl methacrylate is distilled off at a reflux ratio of 1:2 by raising the head temperature from 70° C. to 90° C., whereupon the temperature of the reaction mixture gradually rises to 150° C. The last residues of the unreacted ester are drawn off in vacuum at 130° C. Altogether, 64.5 kg of distillate and 37 kg of a crude product having a content of 92 percent of N-(dimethylaminopropyl)-methacrylamide and one percent of the corresponding Michael-adduct are obtained in addition to high-boiling impurities and the catalyst material.

The crude product is heated for 15 minutes with stirring at 200° C. and subsequently introduced into a vacuum distillation apparatus from which it is distilled at a sump temperature of 145° C.–155° C. and a transfer temperature of 122° C.–128° C. at $4 (10^{-3})$ atmospheres. 33.1 kg of 99.5 percent of N-(dimethylaminopropyl)-methacrylamide are obtained.

EXAMPLE 2

321.5 g (3 mols) of benzylamine, 750 g (7.5 mols) of methyl methacrylate, 0.075 g of 4-methyl-2,6-di-tert.-butyl phenol, and 0.0375 g of phenothiazine are heated to boiling in a 2-liter ground flask with stirring and with the introduction of a little air. Water present is distilled off as a water/methyl methacrylate azeotrope, 10.71 g of dibutyl tin oxide are subsequently introduced at 70° C., the mixture is heated, and the methanol/methyl methacrylate azeotrope which forms is distilled off over a period of five hours. At the conclusion of aminolysis, the crude amide solution is concentrated to dryness in a rotary evaporator, the powdery N-benzyl-methacrylamide is recrystallized from cyclohexane, and then dried in vacuum at 40° C.–50° C. Yield: 456.6 g (about 87 percent of theory); m.p.=83° C.

EXAMPLE 3

297.6 g (3 mols) of cyclohexylamine, 750 g (7.5 mols) of methyl methacrylate, and 0.075 g of 4-methyl-2,6-di-tert-butylphenol and 0.375 g of phenothiazine, as polymerization inhibitors, are heated in a two-liter flask with stirring while blowing in a little air; water present is distilled off as water/methyl methacrylate azeotrope, 10.47 g of dibutyl tin oxide are subsequently added at 70° C., heated, and the methanol/methyl methacrylate azeotrope which forms is distilled off over a period of eight hours. The crystal slurry of N-cyclohexyl-methacrylamide which precipitates on cooling was recrystallized from cyclohexane.

Yield: 317.7 g (ca. 63.4 percent of theory); m.p.=107° C.–108° C.

EXAMPLE 4

200 g (2 mols) of methyl methacrylate and 38.7 g (0.33 mol) of hexamethylendiamine were reacted in the presence of 2 g of dibutyl tin oxide and 100 ppm of hydroquinone for ten hours at the boiling temperature, whereby the methanol formed was continuously distilled off as the methanol/methyl methacrylate azeotrope. Thereafter, no free amine could be demonstrated to be present in the reaction mixture. The hexamethylene-bis-methacrylamide was formed with a selectivity of 68 percent and could be recrystallized from an acetic acid-hexane mixture or from toluene.

m.p.=95° C.

EXAMPLE 5

600 g (6 mols) of methyl methacrylate and 140 g (1.5 mols) of aniline are reacted in the presence of 6 g of dibutyl tin oxide and a stabilizer for 18 hours at the boiling temperature (ca. 105° C.), during which the methanol formed is continuously distilled off as a methanol/methyl methacrylate azeotrope.

Conversion (calculated on the aniline)=80 percent;
Selectivity is above 90 percent.

The crude methacrylic acid anilide is purified by recrystallization from benzene or by vacuum distillation.

m.p.=85° C.–87° C.

EXAMPLE 6

800 g of methyl methacrylate, 10.04 g of dioctyl tin oxide, 0.08 g of 4-methyl-2,6-di-tert.-butyl phenol, and 0.4 g of phenothiazine are heated to boiling in a round flask while stirring and with the introduction of a little air. 204 g of dimethylaminopropylamine are slowly added dropwise. At the same time, the methanol/methyl methacrylate azeotrope which is formed is drawn off at a reflux ratio of 2.5:1 until a head temperature of 75° C. is reached. After addition is concluded, the mixture is permitted to post-react for several hours and then the remaining methanol and methyl methacrylate are drawn off as an azeotrope at a reflux ratio of 2.5:1 until only pure methyl methacrylate distills off. 94.5 percent of the calculated amount of methanol is found in the distillate.

The crude ester solution is concentrated in a rotary evaporator and the crude amine is subsequently heated for about 15 minutes at 200° C. After the distillation, 285 g of dimethylaminopropylmethylacrylamide with a purity of 99 percent are obtained.

EXAMPLE 7

321.5 g of benzyl amine, 1066.5 g of n-butyl methacrylate, and 0.0533 g of phenothiazine are heated to boiling in a round flask with the introduction of air; any water possibly present is distilled off as an azeotrope with butyl methacrylate. 13.88 g of dioctyl tin oxide are added at a sump temperature of 80° C. and, after heating, a butanol/butyl methacrylate azeotrope is distilled off within a period of several hours over the head until only pure butyl methacrylate comes off. The crude amide solution is concentrated in a rotary evaporator and the precipitating powder is recrystallized from cyclohexane. After drying, 420 g of benzylmethacrylamide (80% of theory) having a melting point of 83° C. are obtained.

What is claimed is:

1. The method for making an N-substituted acrylamide or an N-substituted methacrylamide which comprises reacting an alkyl ester of acrylic acid or of methacrylic acid with an aliphatic amine or with an aromatic amine at a temperature between 50° C. and 180° C. in the presence of a catalytic amount of a dialkyl tin oxide.

2. A method as in claim 1 wherein said ester is an alkyl methacrylate having 1 to 4 carbon atoms in the alkyl portion.

3. A method as in claim 1 wherein each alkyl group in said dialkyl tin oxide has 4 to 8 carbon atoms.

* * * * *